US00PP28759P2

(12) United States Plant Patent
Hansen

(10) Patent No.: US PP28,759 P2
(45) Date of Patent: Dec. 12, 2017

(54) ***LAGERSTROEMIA* PLANT NAMED 'SWEET MACCHIATO'**

(50) Latin Name: *Lagerstroemia indica*
Varietal Denomination: Sweet Macchiato

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 22 days.

(21) Appl. No.: 14/999,717

(22) Filed: Jun. 17, 2016

(51) Int. Cl.
*A01H 5/00* (2006.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen Redden

(57) ABSTRACT

The new and distinct crape myrtle plant named *Lagerstroemia* 'Sweet Macchiato' has a short rounded habit, is ground hardy to at least USDA zone 6, has glossy reddish mahogany foliage that develops to a dark olive green color. The flowers are fragrant, large and hot-pink colored.

2 Drawing Sheets

Botanical classification: *Lagerstroemia indica.*
Varietal denomination: 'Sweet Macchiato'.

BACKGROUND OF THE INVENTION

The present invention relates to a new and distinct cultivar of the ornamental flowering shrub *Lagerstroemia indica* commonly known as crape myrtle, and hereafter referred to by the cultivar name 'Sweet Macchiato'.

*Lagerstroemia* 'Sweet Macchiato' originated from open-pollinated seed of *Lagerstroemia* 'Whit VI' U.S. Plant Pat. No. 14,438 collected by the inventor in the fall of 2010 at a cultivated area in Raleigh, N.C., USA. The new plant was grown out in a full-sun, loamy-sand field environment with water as needed and passed rigorous evaluations at the same nursery with goals for this program to produce improved, garden-worthy plants for the ornamental plant market of quality flower color and improved habit that would withstand cold temperatures. The single new plant meeting these criteria was originally assigned breeder code H10-02-28.

No plants of *Lagerstroemia* 'Sweet Macchiato' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Lagerstroemia* 'Sweet Macchiato' was first asexually propagated from a single select plant in 2012 by stem cuttings at a wholesale perennial nursery in Zeeland, Mich. The resultant asexually propagated plants have been found to be stable and true to type in successive generations of asexual reproduction.

SUMMARY OF THE INVENTION

Plants of the new crape myrtle cultivar *Lagerstroemia* 'Sweet Macchiato' have not been observed under all possible environmental conditions. The phenotype may vary somewhat with variations in environment such as light-intensity, temperature light-intensity, available moisture and fertility without, however, any variance in genotype.

The following traits in combination have been consistently observed and are determined to make up some of the unique characteristics of 'Sweet Macchiato':

1. Short rounded habit;
2. Ground hardy to at least USDA zone 6;
3. Glossy foliage emerges reddish mahogany and develops to a dark olive coloring;
4. Fragrant hot-pink flowers.

The nearest comparison crape myrtle varieties known to the inventor are: 'Coral Filli' U.S. Plant Pat. No. 14,317, 'Rosey Carpet' U.S. Plant Pat. No. 13,965, 'Plum Magic' U.S. Plant Pat. No. 23,518 and 'Coral Magic' U.S. Plant Pat. No. 23,922. Compared to 'Coral Filli' the new plant is shorter in habit and the flower color is more toward a lavender hue. Compared to 'Rosey Carpet' the new plant is taller and more mounded in habit, and the flower color is more in the lavender hue and slightly less pink. Compared to 'Plum Magic' the new plant is shorter and more mounded in habit, and the flower color is lighter in hue. Compared to 'Coral Magic' the new plant is significantly shorter in height and the petals are more in the lavender range.

Compared to the female parent, 'Whit VI', the new plant is significantly shorter and has flowers that are hot-pink colored rather than the height of over 400 cm with white flowers.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
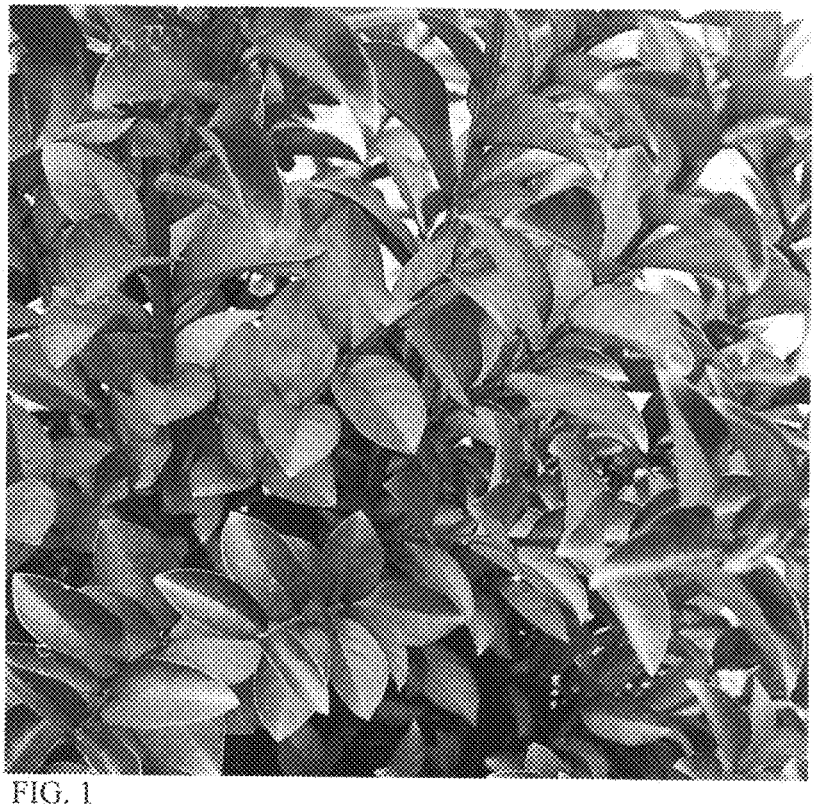
FIG. 1 shows a close-up of the foliage and young stems.
Figure 2:
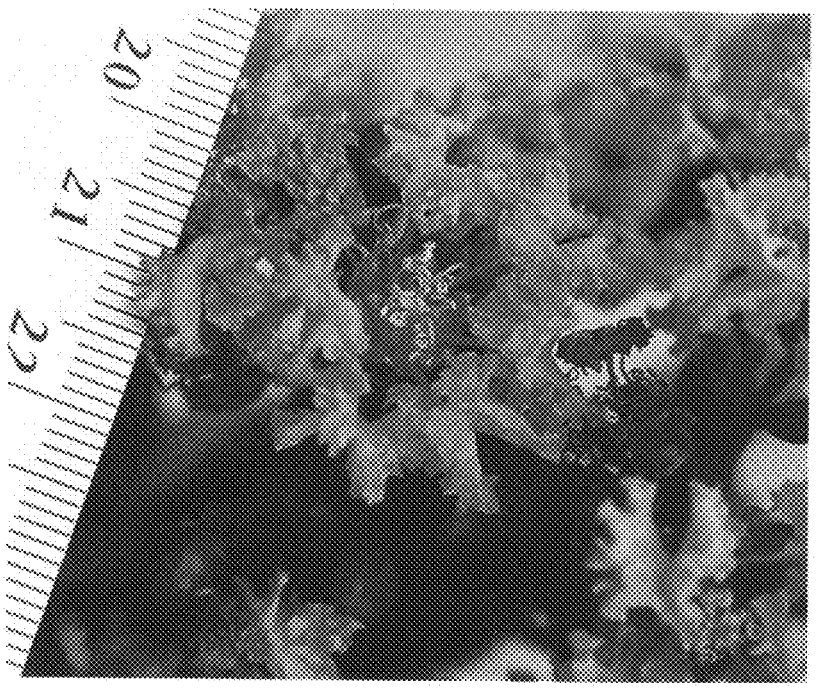
FIG. 2 shows a close-up of the flowers.
Figure 3:
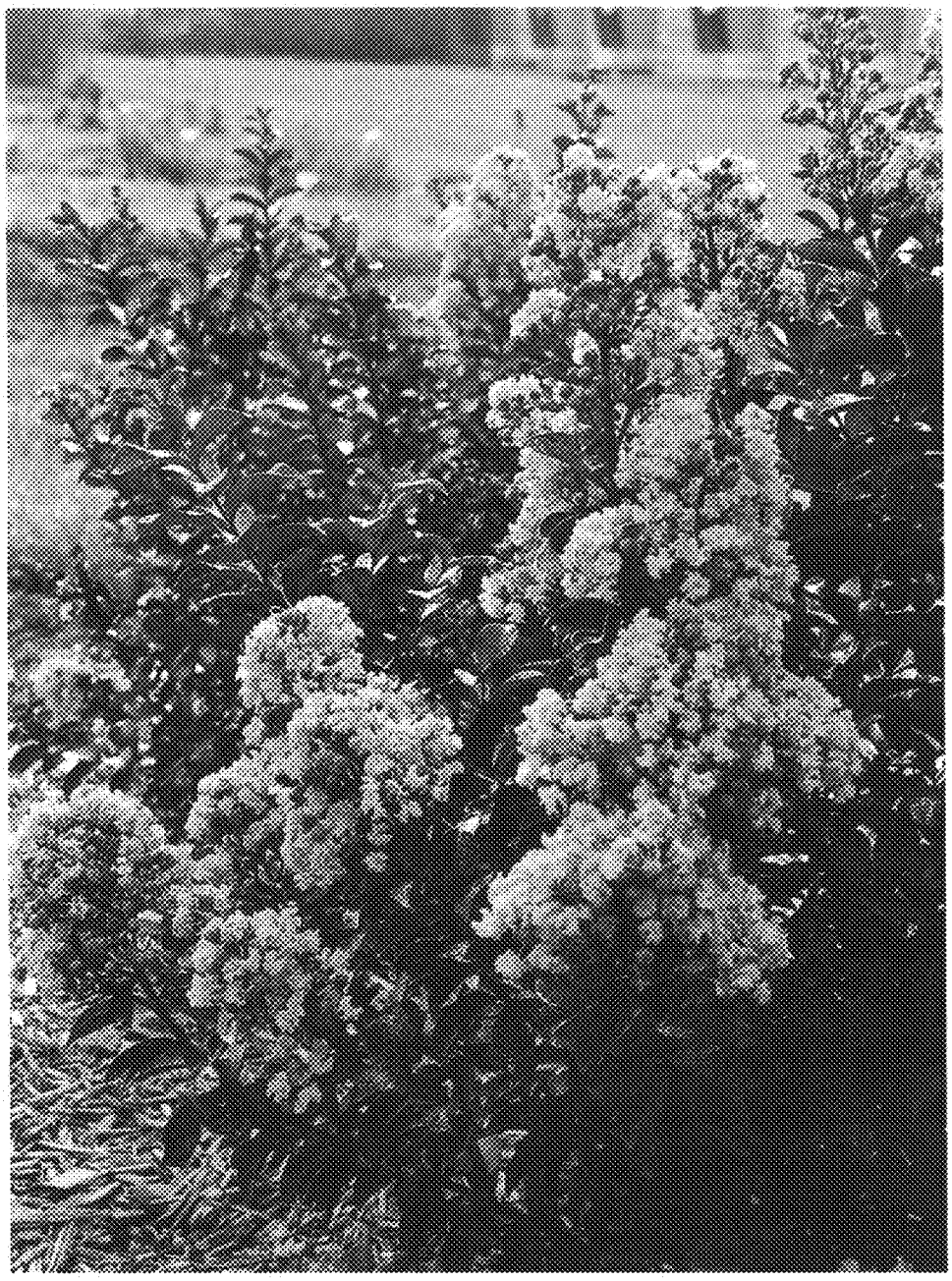
FIG. 3 shows the habit of a three-year-old plant in mid-season flowering.

The following botanical descriptions and color references are based on the 2001 edition of The Royal Horticultural Society Colour Chart except where common dictionary terms are used. Descriptions are based on two-year-old plants growing in a full-sun, trial garden with supplemental fertilizer and water as needed.

Plant description:

*Habit*.—Mounded with extensive branching.

*Plant size*.—Average about 45.0 cm tall and about 43.0 cm across about 20.0 cm above soil line.

*Stems*.—Two main stems per plant; terete at base, average about 9.0 mm diameter at base; young stems slightly puberulent, with four longitudinal carinae giving appearance of squaring, about 3.0 mm diameter toward apex; older basal stem exfoliating; attitude mostly upright.

*Stem color*.—Young stems and carina with intense light nearest RHS 187B, shaded and undersides of young stems nearest RHS 146C; basal older woody stems combinations of nearest RHS 199D and nearest RHS N199B.

*Branches*.—Average 16 per main stem; to about 30.0 cm long; attitude upright to outward.

*Nodes*.—About 21 nodes per main stem, average internode length about 8.0 mm.

*Node color*.—Same as surrounding stem.

*Leaves*.—Elliptical; apex acute; base cuneate; margin entire, ciliolate; both surfaces laevigate and glabrous; sub-opposite.

*Young leaf color*.—Adaxial blend of RHS 178A and RHS 183A; abaxial nearest RHS 175A.

*Mature leaf color*.—Adaxial nearest RHS 147A; abaxial nearest RHS 137C.

*Veins*.—Pinnate; micro-puberulent adaxial and sparsely abaxial.

*Adaxial vein color*.—Young leaf nearest RHS 178A; mature leaf midrib nearest RHS 186C with lateral veins having undertones or nearest RHS 147A.

*Abaxial vein color*.—Young leaf nearest RHS 175A, mature leaf nearest RHS 160D with tinting nearest RHS 184B.

*Petiole*.—Puberulent abaxial and adaxial; adaxial slightly applanate; about 1.0 mm long and about 2.0 mm wide.

*Petiole color*.—Adaxial and abaxial nearest RHS 187A on young expanding leaves; adaxial and abaxial between RHS N186C and RHS 183A.

*Inflorescence*.—Panicle; average about 40 flowers; terminal panicles up to 120 flowers; up to about 14.0 cm long and about 13.0 cm across; beginning late-summer and continuing until fall, for about eight weeks.

*Buds*.—Globose; laevigate; glabrous; about 7.0 mm tall and 6.0 mm diameter one day prior to opening.

*Bud color*.—Nearest RHS 144C at basal one-third, between RHS 178A and RHS 178B above.

*Flowers*.—Perfect; regular; actinomorphic; individually about 2.8 cm across and about 1.6 cm tall; lasting about two days.

*Flower fragrance*.—Sweet, light.

*Peduncle*.—Terete with four longitudinal carinae; about 3.5 mm diameter at base, about 14.0 cm long.

*Peduncle color*.—Nearest RHS 187B.

*Pedicel*.—Terete, about 3.0 mm long and 1.0 mm diameter.

*Pedicel color*.—Nearest RHS 187B.

*Sepals*.—Fused in the basal 2.5 mm; acute apex, entire margin; glabrous and laevigate both adaxial and abaxial; about 5.5 mm long and individually about 3.0 mm long above the fusion and about 3.0 mm wide at fusion point.

*Sepal color*.—Adaxial base nearest RHS 145B, distally nearest RHS 185D; abaxial base nearest RHS 138B, distally nearest RHS 187C.

*Petals*.—Six; stalked; glabrous; blade ruffled or crisped; margin crisped; blade with rounded apex and cordate to sagittate base, to about 1.0 cm across and 1.0 cm long; claw base adnate to sepal, claw about 6.0 mm long and 0.6 mm diameter; overall about 1.6 cm long.

*Petal color*.—Blade adaxial and abaxial nearest RHS 71D when first opening and becoming between RHS 71A and RHS 71B before dehiscing; claw nearest RHS 180B.

*Androecium*.—Stamens: total about 42; six longer and about 36 shorter. Filaments: longer stamens to about 15.0 mm long and about 0.5 mm diameter, curled about 180 degrees in last 5.0 mm; shorter filaments nearly straight, about 9.0 mm long and less than 0.3 mm diameter; color of longer filaments between RHS 180D and RHS 180C, color shorter filaments nearest RHS 145B toward apex and nearest RHS 65C toward base. Anthers: oblong; more developed on longer stamens to about 1.5 mm long and 1.0 mm across, on shorter stamens about 1.0 mm long and about 0.5 mm across; color nearest RHS N187A. Pollen: abundant on longer stamens; color nearest RHS 10C.

*Gynoecium*.—One. Style: terete; glabrous; about 12.0 mm long and 1.0 mm diameter; color between RHS 180A and RHS 179A in the middle portion, distally nearest RHS 2C and base nearest RHS 2D. Stigma: globose; about 1.2 mm diameter; color nearest RHS 187A. Ovary: superior; globose; about 2.0 mm tall and 2.0 mm diameter; color nearest RHS 145C.

*Fruit*.—Globose; six-valved dehiscent capsule; about 7.0 mm wide and 7.0 mm tall; apex rostrate; base rounded.

*Fruit color*.—Between RHS 200B and RHS 200A.

*Seed*.—Lunate; about 5.0 mm long and 2.0 mm across at widest point.

*Seed color*.—Between RHS 165B and RHS 165C.

Disease resistance: *Lagerstroemia* 'Sweet Macchiato' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

I claim:

1. A new and distinct cultivar of crape myrtle plant named *Lagerstroemia* 'Sweet Macchiato' essentially as herein illustrated and described.

* * * * *